(12) United States Patent
Kawano

(10) Patent No.: US 9,931,022 B2
(45) Date of Patent: Apr. 3, 2018

(54) CAPSULE MEDICAL DEVICE GUIDANCE SYSTEM

(71) Applicant: OLYMPUS CORPORATION, Tokyo (JP)

(72) Inventor: Hironao Kawano, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/343,986

(22) Filed: Nov. 4, 2016

(65) Prior Publication Data

US 2017/0049303 A1 Feb. 23, 2017

Related U.S. Application Data

(63) Continuation of application No. PCT/JP2015/062657, filed on Apr. 27, 2015.

(30) Foreign Application Priority Data

Aug. 8, 2014 (JP) .................................. 2014-163115

(51) Int. Cl.
*A61B 1/04* (2006.01)
*A61B 1/00* (2006.01)
(Continued)

(52) U.S. Cl.
CPC ............ *A61B 1/00158* (2013.01); *A61B 1/00* (2013.01); *A61B 1/00006* (2013.01);
(Continued)

(58) Field of Classification Search
CPC ....... A61B 1/00039; A61B 1/04; A61B 1/041; A61B 1/00009; A61B 1/00045;
(Continued)

(56) References Cited

U.S. PATENT DOCUMENTS

| 8,469,879 B2 | 6/2013 | Uchiyama |
| 2004/0236180 A1 | 11/2004 | Uchiyama et al. |

(Continued)

FOREIGN PATENT DOCUMENTS

| CN | 102421350 A | 4/2012 |
| CN | 102578992 A | 7/2012 |

(Continued)

OTHER PUBLICATIONS

International Search Report dated Jun. 30, 2015 issued in PCT/JP2015/062657.

(Continued)

*Primary Examiner* — John P Leubecker
(74) *Attorney, Agent, or Firm* — Scully, Scott, Murphy & Presser, P.C.

(57) ABSTRACT

A capsule medical device guidance system includes: an imaging unit arranged inside a capsule medical device; a guidance unit configured to guide the capsule medical device inside a subject; a display unit including a screen is displayed; a first operation input unit configured to input first instruction information for changing at least one of a position and a posture of the capsule medical device; a second operation input unit configured to input second instruction information for rotating within the screen, the image displayed on the screen, around a center of the image; a guidance controller configured to control the guidance unit so as to change at least one of the position and the posture of the capsule medical device, based on the first instruction information; and a display controller configured to control a direction of the image displayed on the screen based on the second instruction information.

10 Claims, 10 Drawing Sheets

(51) Int. Cl.
*A61B 5/07* (2006.01)
*A61B 1/045* (2006.01)

(52) U.S. Cl.
CPC ...... *A61B 1/00016* (2013.01); *A61B 1/00039* (2013.01); *A61B 1/00045* (2013.01); *A61B 1/04* (2013.01); *A61B 1/041* (2013.01); *A61B 1/045* (2013.01); *A61B 5/07* (2013.01)

(58) Field of Classification Search
CPC ............ A61B 1/00006; A61B 1/00158; A61B 2034/733; A61B 5/6861; A61B 5/06
See application file for complete search history.

(56) References Cited

U.S. PATENT DOCUMENTS

| | | | |
|---|---|---|---|
| 2006/0015012 A1* | 1/2006 | Sato | A61B 1/00006 600/118 |
| 2007/0191683 A1 | 8/2007 | Fujimori | |
| 2007/0219405 A1 | 9/2007 | Uchiyama et al. | |
| 2007/0299301 A1* | 12/2007 | Uchiyama | A61B 1/0008 600/101 |
| 2008/0312501 A1 | 12/2008 | Hasegawa et al. | |
| 2009/0043155 A1 | 2/2009 | Fujimori | |
| 2009/0177032 A1* | 7/2009 | Garibaldi | A61B 1/00158 600/109 |
| 2009/0227864 A1* | 9/2009 | Sato | A61B 1/0005 600/424 |
| 2010/0010305 A1* | 1/2010 | Kawano | A61B 1/0005 600/118 |
| 2010/0030026 A1 | 2/2010 | Uchiyama et al. | |
| 2011/0196201 A1 | 8/2011 | Sato et al. | |
| 2012/0116162 A1* | 5/2012 | Kawano | A61B 1/00158 600/118 |
| 2012/0203068 A1 | 8/2012 | Sato et al. | |
| 2012/0238809 A1 | 9/2012 | Sato et al. | |
| 2015/0065801 A1 | 3/2015 | Chiba et al. | |

FOREIGN PATENT DOCUMENTS

| | | |
|---|---|---|
| JP | 2001-017388 A | 1/2001 |
| JP | 2004-255174 A | 9/2004 |
| JP | 2006-218027 A | 8/2006 |
| JP | 2006-288832 A | 10/2006 |
| JP | 2007-000608 A | 1/2007 |
| JP | 2007-006974 A | 1/2007 |
| JP | 2007-283001 A | 11/2007 |
| JP | 2009-066033 A | 4/2009 |
| JP | 2009213613 A | 9/2009 |
| JP | 2009-240405 A | 10/2009 |
| JP | 5458225 B1 | 4/2014 |

OTHER PUBLICATIONS

Japanese Office Action dated Feb. 26, 2016 issued in Japanese Patent Application No. 2015-558049.
English abstract of WO 2013/168710 dated Nov. 14, 2013.
Chinese Office Action dated Aug. 15, 2017 in Chinese Patent Application No. 201580025295.0.

* cited by examiner

UPWARD DIRECTION

UPWARD DIRECTION

CAPSULE MEDICAL DEVICE GUIDANCE SYSTEM

CROSS-REFERENCE TO RELATED APPLICATIONS

This application is a continuation of PCT international application Ser. No. PCT/JP2015/062657 filed on Apr. 27, 2015 which designates the United States, incorporated herein by reference, and which claims the benefit of priority from Japanese Patent Application No. 2014-163115, filed on Aug. 8, 2014, incorporated herein by reference.

BACKGROUND

1. Technical Field

The disclosure relates to a capsule medical device guidance system for guiding a capsule medical device that is introduced into a subject.

2. Related Art

Conventionally, capsule medical devices which are introduced into a subject to acquire various types of information on the inside of the subject or deliver a medicine or the like into the subject have been developed. As an example, a capsule endoscope which is formed in such a size that can be introduced into the gastrointestinal tract of a subject is known.

A capsule endoscope is a device which has an imaging function and a wireless communication function inside a capsule-shaped casing. The capsule endoscope acquires image data by capturing of an image (hereinafter referred to as an in-vivo image) of the inside of an organ of a subject while moving through the gastrointestinal tract by the peristaltic movement or the like after being swallowed into the subject and wirelessly transmits the image data sequentially. The wirelessly transmitted image data is received by a receiving device provided outside the subject, imported to an image display device of a workstation or the like, and subjected to prescribed image processing. In this way, the in-vivo image of the subject can be displayed as a still-image or a video image.

In recent years, a guidance system that guides a capsule endoscope introduced into a subject using a magnetic field has been proposed. This guidance system is configured such that a user can operate guidance of a capsule endoscope using an operation input device while referring to an in-vivo image based on the image data wirelessly transmitted from the capsule endoscope.

For example, JP 2009-66033 A discloses a capsule guidance system including a capsule endoscope which has an imaging element that captures an in-vivo image of a subject and a magnet having a magnetization direction relatively fixed with respect to the imaging element, a magnetic guidance device that applies a magnetic field to the magnet to guide the capsule endoscope according to a magnetic force, and a display unit that displays the in-vivo image acquired by the imaging element included in the capsule endoscope. In JP 2009-66033 A, when the magnetic guidance device is controlled to apply a magnetic field of a reference direction to the magnet in the capsule endoscope, and the magnet is magnetized in the reference direction following the magnetic field of the reference direction, a rotation angle of an image captured by the imaging element is initialized, the rotation of subsequent in-vivo images is corrected based on the image, and the in-vivo images of which the rotation is corrected are sequentially displayed on the display unit.

Moreover, JP 2004-255174 A discloses a capsule medical device guidance system including a capsule body in which a spiral projection is formed on an outer circumferential surface and a magnet is provided therein and a rotating magnetic field generator disposed outside a subject. In JP 2004-255174 A, when an operation instruction is input to the system, the rotating magnetic field generator generates a rotating magnetic field of the instructed direction and stores information such as the direction or the like of the rotating magnetic field. When an operation or the like of changing a moving direction of the capsule body is input, the moving direction of the capsule body is changed by continuously changing the state of the rotating magnetic field based on the stored information.

SUMMARY

In some embodiments, a capsule medical device guidance system for guiding a capsule medical device configured to be introduced into a subject to capture an inside of the subject is provided. The capsule medical device guidance system includes: an imaging unit that is fixedly arranged inside the capsule medical device, the imaging unit being configured to capture the inside of the subject; a guidance unit configured to guide the capsule medical device inside the subject; a display unit including a screen on which an image captured by the imaging unit is displayed; a first operation input unit configured to input first instruction information for changing at least one of a position and a posture of the capsule medical device according to an external input operation; a second operation input unit configured to input second instruction information for rotating within the screen, the image displayed on the screen, around a center of the image according to an external input operation; a guidance controller configured to control the guidance unit so as to change at least one of the position and the posture of the capsule medical device, based on the first instruction information; and a display controller configured to control a direction of the image displayed on the screen based on the second instruction information. When the first instruction information is input, the guidance controller is configured to control the guidance unit, based on an arrangement of the imaging unit in the capsule medical device and the direction of the image displayed on the screen, so that a relation between a direction of a change in a visual field of the image displayed on the screen and an operation input that is input on the first operation input unit is constant regardless of the direction of the image.

In some embodiments, a capsule medical device guidance system for guiding a capsule medical device configured to be introduced into a subject to capture an inside of the subject is provided. The capsule medical device guidance system includes: an imaging unit that is fixedly arranged inside the capsule medical device, the imaging unit being configured to capture the inside of the subject; a guidance unit configured to guide the capsule medical device inside the subject; a display unit including a screen on which an image captured by the imaging unit is displayed; a first operation input unit configured to input first instruction information for changing at least one of a position and a posture of the capsule medical device according to an external input operation; a guidance controller configured to control the guidance unit so as to change at least one of the position and the posture of the capsule medical device, based on the first instruction information; and a display controller configured to: determine whether an angle between a direction orthogonal to a imaging direction of the imaging unit and indicating an upper side of the imaging unit and a vertically upward direction is an obtuse angle; and if the angle is determined to be the obtuse angle, display a notification icon on the screen, and if the angle is determined not to be the obtuse angle, hide the notification icon on the screen or display, on the screen, a notification icon different from the notification icon when the angle is determined to be the obtuse angle.

The above and other features, advantages and technical and industrial significance of this invention will be better understood by reading the following detailed description of presently preferred embodiments of the invention, when considered in connection with the accompanying drawings.

DETAILED DESCRIPTION

Figure 1:
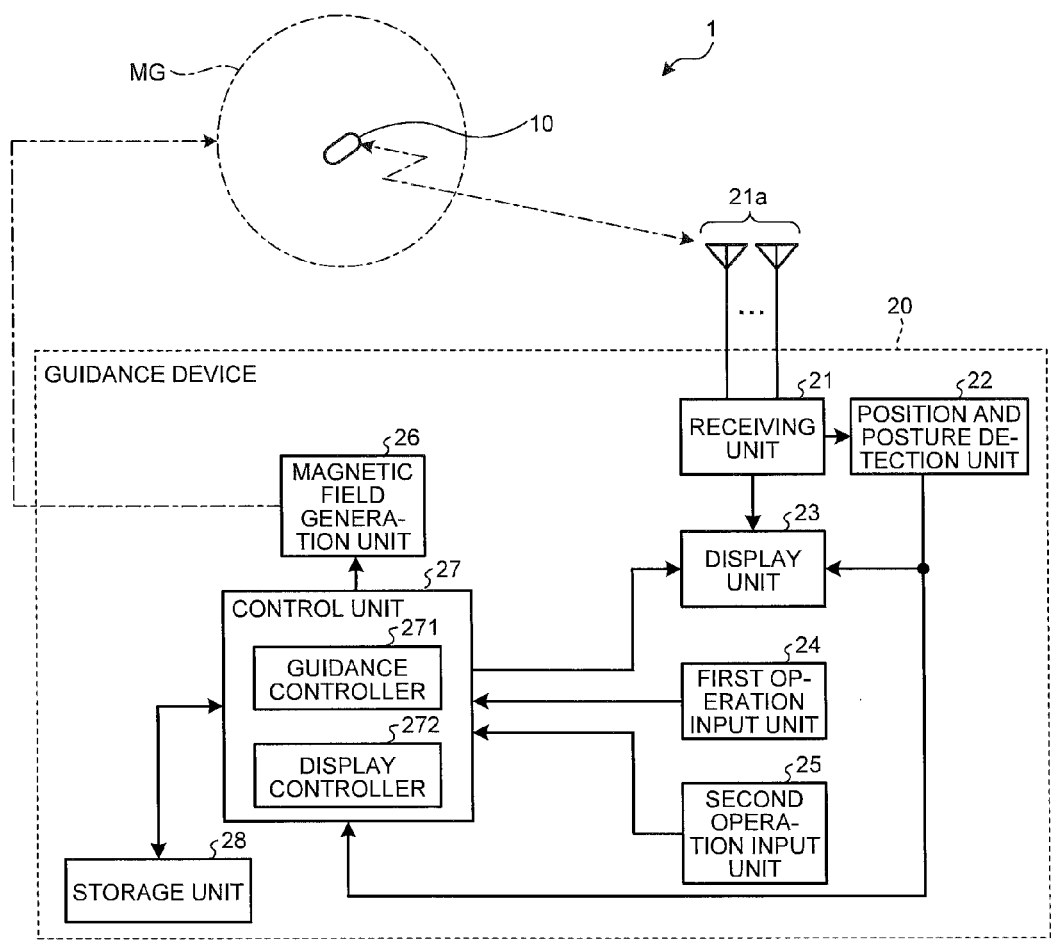
FIG. 1 is a diagram illustrating a configuration example of a capsule medical device guidance system according to a first embodiment of the disclosure.

A capsule medical device guidance system according to embodiments of the disclosure will be described below with reference to the drawings. In the following description, although a capsule endoscope that is orally introduced into a subject and captures an image of the inside (the lumen) of the subject is illustrated as a form of a capsule medical device which is guided by the capsule medical device guidance system according to the present embodiment, the present invention is not limited to this embodiment. That is, for example, the present invention can be applied to various medical devices which are used by being inserted into a subject, such as a capsule medical device that delivers medicine or the like into a subject or a capsule medical device having a PH sensor that measures the PH inside a subject in addition to a capsule endoscope that captures the lumen and moves in the lumen from the esophagus to the anus of a subject.

In the following description, the shape, the size, and the positional relationship in the respective drawings are schematically illustrated to such an extent that facilitates understanding of the content of the present invention. Therefore, the present invention is not limited to the shape, the size, and the positional relationship illustrated in each drawing. In the description of the drawings, the same constituent elements and portions are denoted by the same reference numerals.

First Embodiment

FIG. 1 is a schematic view illustrating a configuration example of a capsule medical device guidance system according to the first embodiment of the disclosure. As illustrated in FIG. 1, a capsule medical device guidance system 1 according to the first embodiment includes a capsule endoscope 10 as an example of a capsule medical device and a guidance device 20 that guides the capsule endoscope 10 introduced into a subject. In the first embodiment, a system in which a permanent magnet is provided inside the capsule endoscope 10 to apply a magnetic field MG to the capsule endoscope 10 to guide the capsule endoscope 10 is used.

The capsule endoscope 10 moves through the gastrointestinal tract after being introduced into the subject together with a prescribed liquid through oral ingestion or the like and is finally discharged outside the subject. In this period, the capsule endoscope 10 floats in the liquid inside an organ such as the stomach or the like, for example, captures the images of the inside of the subject while being guided by the magnetic field MG, sequentially generates the image data of the in-vivo images, and wirelessly transmits the image data.

Figure 2:
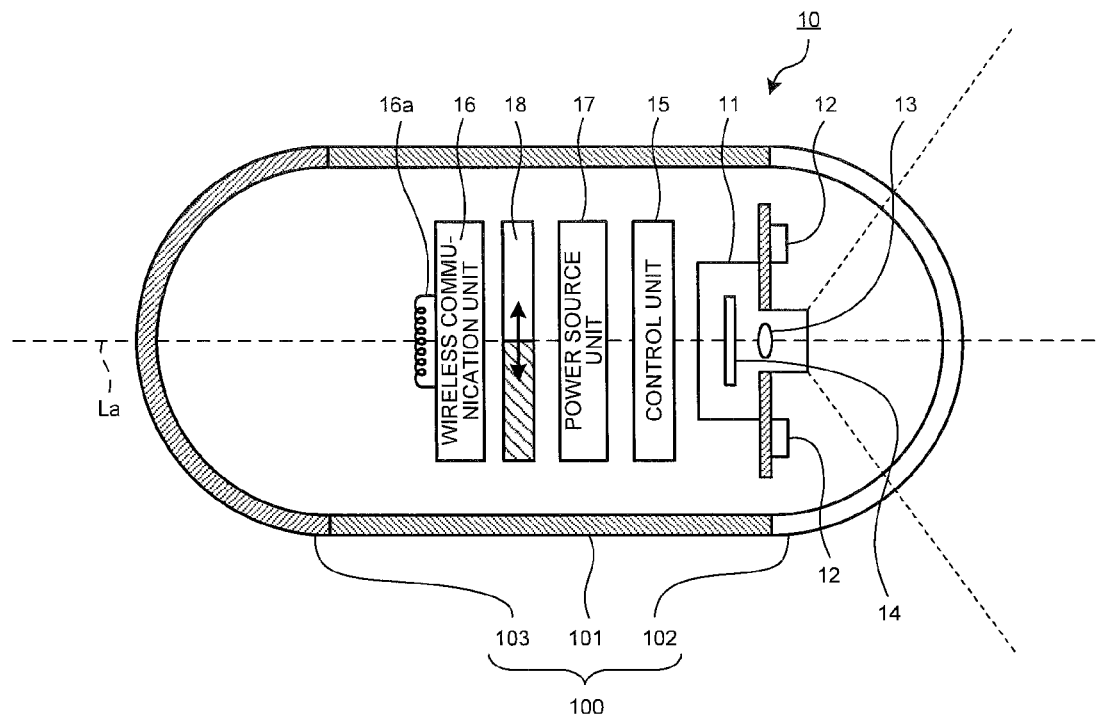
FIG. 2 is a schematic view illustrating an example of an inner structure of a capsule endoscope illustrated in FIG. 1.

FIG. 2 is a schematic view illustrating an example of an inner structure of the capsule endoscope 10. As illustrated in FIG. 2, the capsule endoscope 10 includes a capsule-shaped casing 100 which is an outer casing formed in such a size that can be easily introduced into an organ of a subject, an imaging unit 11 that captures the inside of the subject to output an image signal, a control unit 15 that processes the image signal output from the imaging unit 11 and controls respective constituent units of the capsule endoscope 10, a wireless communication unit 16 that wirelessly transmits the signal processed by the control unit 15 to the outside of the capsule endoscope 10, a power source unit 17 that supplies electric power to the respective units of the capsule endoscope 10, and a permanent magnet 18 for enabling the guidance device 20 to perform guidance.

The capsule-shaped casing 100 is an outer casing which includes a tubular casing 101 and dome-shaped casings 102 and 103 and is formed in such a size that can be introduced into the organ of a subject. The capsule-shaped casing 100 is formed by closing both opening ends of the tubular casing 101 with the dome-shaped casings 102 and 103. The tubular casing 101 and the dome-shaped casing 103 are color casings that are substantially opaque to visible light. On the other hand, the dome-shaped casing 102 is a dome-shaped optical member that is transparent to light in a prescribed wavelength range such as visible light. As illustrated in FIG. 2, such the capsule-shaped casing 100 liquid-tightly contains the imaging unit 11, the control unit 15, the wireless communication unit 16, the power source unit 17, and the permanent magnet 18.

The imaging unit 11 includes an illumination unit 12 such as an LED, an optical system 13 such as a condenser lens, and an imaging element 14 such as a CMOS image sensor or a CCD. The illumination unit 12 emits illumination light such as white light to an imaging visual field of the imaging element 14 and illuminates the subject in the imaging visual field over the dome-shaped casing 102. The optical system 13 condenses light reflected from the imaging visual field and condenses and forms an image on an imaging surface of the imaging element 14. The imaging element 14 converts the reflection light (optical signal) from the imaging visual field formed on the imaging surface to an electrical signal and outputs the electrical signal as an image signal.

The control unit 15 controls the respective operations of the imaging unit 11 and the wireless communication unit 16 and controls the input and output of signals between these respective constituent units. Specifically, the control unit 15 allows the subject in the imaging visual field illuminated by the illumination unit 12 to be captured by the imaging element 14. Moreover, the control unit 15 applies predetermined image processing to the image signal output from the imaging element 14. Furthermore, the control unit 15 causes the wireless communication unit 16 to wirelessly transmit the image signal sequentially in a chronological order.

The wireless communication unit 16 includes an antenna 16a for transmitting radio signal. The wireless communication unit 16 acquires the image signal of the in-vivo image generated by the imaging unit 11 capturing the subject from the control unit 15 and performs a modulation process or the like on the image signal to generate a radio signal. The wireless communication unit 16 transmits the generated radio signal via the antenna 16a.

The power source unit 17 is an electric storage unit such as a button battery or a capacitor and includes a switch unit such as a magnetic switch or an optical switch. When the power source unit 17 is configured to include a magnetic switch, the power source unit 17 switches between ON and OFF states of the power source according to a magnetic field applied from the outside. In the ON state, the power source unit 17 appropriately supplies the electric power of the electric storage unit to the imaging unit 11, the control unit 15, and the wireless communication unit 16 which are the constituent units of the capsule endoscope 10. In the OFF state, the power source unit 17 stops the supply of electric power to the respective constituent units.

The permanent magnet 18 is provided to enable the guidance of the capsule endoscope 10 according to the magnetic field MG generated by a magnetic field generation unit 26 described later and is fixedly arranged inside the capsule-shaped casing 100 so that the magnetization direction thereof is inclined with respect to a long axis La. In FIG. 2, the magnetization direction of the permanent magnet 18 is indicated by an arrow. In the first embodiment, the permanent magnet 18 is disposed so that the magnetization direction is orthogonal to the long axis La. The permanent magnet 18 changes its position and posture following the magnetic field applied from the outside. In this way, the guidance of the capsule endoscope 10 by the magnetic field generation unit 26 is realized.

Figure 3:
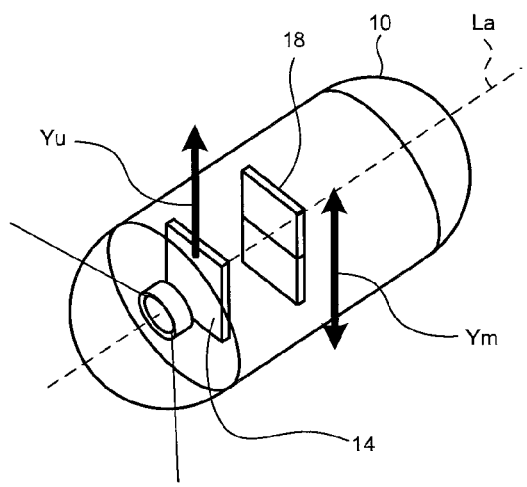
FIG. 3 is a schematic view for describing a relative positional relation between an imaging element and a permanent magnet inside the capsule endoscope.

FIG. 3 is a schematic view for describing a relative positional relation between the imaging element 14 and the permanent magnet 18. The permanent magnet 18 is fixedly arranged inside the capsule-shaped casing 100 in a state of being relatively fixed with respect to the imaging unit 11. More specifically, the permanent magnet 18 is arranged so that the magnetization direction is relatively defined with respect to the up-down direction of the imaging surface of the imaging element 14. In FIG. 3, the permanent magnet 18 is arranged so that a magnetization direction Ym thereof is parallel to an up-down direction Yu of the imaging surface of the imaging element 14.

Figure 4:
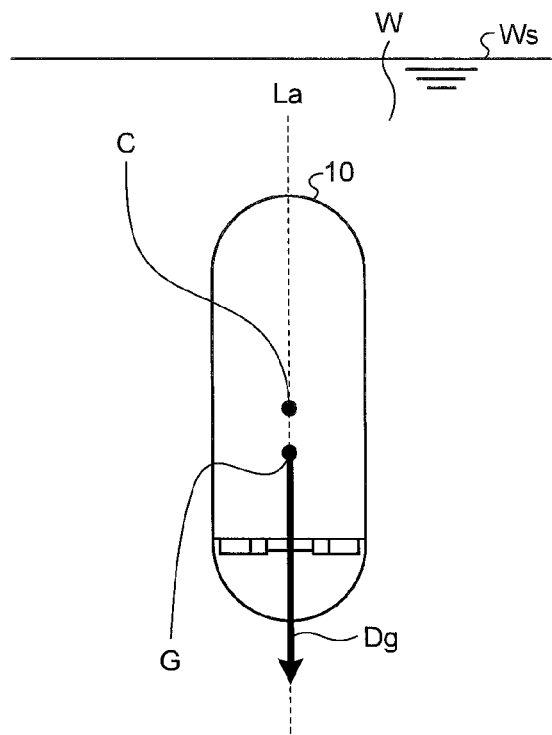
FIG. 4 is a conceptual diagram for describing a state of the capsule endoscope in which liquid is introduced into a subject (a state in which a magnetic field does not act)

FIG. 4 is a conceptual diagram for describing the state of the capsule endoscope 10 in which a liquid W is introduced into a subject. The capsule endoscope 10 illustrated in the first embodiment is designed so as to have a smaller specific gravity than the specific gravity of the liquid W and to float in the liquid W in a state in which the magnetic field from the magnetic field generation unit 26 does not act. Moreover, the center of gravity G of the capsule endoscope 10 is on the long axis La of the capsule endoscope 10 and is shifted from the geometric center C of the capsule endoscope 10. In the first embodiment, the center of gravity G of the capsule endoscope 10 is set to a position which is on the long axis La and is shifted from the geometric center C of the capsule-shaped casing 100 toward the imaging unit 11 by adjusting the positions of the respective constituent units such as the power source unit 17 and the permanent magnet 18. Due to this, the capsule endoscope 10 floats in the liquid W in a state in which the long axis La thereof is maintained to be approximately parallel to the vertical direction (the direction of gravity) Dg. In other words, the capsule endoscope 10 floats in the liquid W in a state in which a line connecting the geometric center C and the center of gravity G is upright. The capsule endoscope 10 faces the imaging visual field of the imaging unit 11 vertically downward in such an upright posture. The liquid W is a liquid that is harmless to the human body such as water or physiological salt solution.

As described above, the permanent magnet 18 illustrated in FIG. 3 is disposed so that the magnetization direction Ym thereof is orthogonal to the long axis La. That is, the magnetization direction Ym of the permanent magnet 18 is identical to the radial direction of the capsule endoscope 10. Therefore, when a magnetic field for controlling the position and the posture of the capsule endoscope 10 does not act on the permanent magnet 18, the capsule endoscope 10 floats in the liquid W in a state in which the magnetization direction Ym is identical to a horizontal direction. In this case, a plane which passes through the magnetization direction Ym and the line connecting the geometric center C and the center of gravity G of the capsule-shaped casing 100 is a vertical plane.

Figure 5:
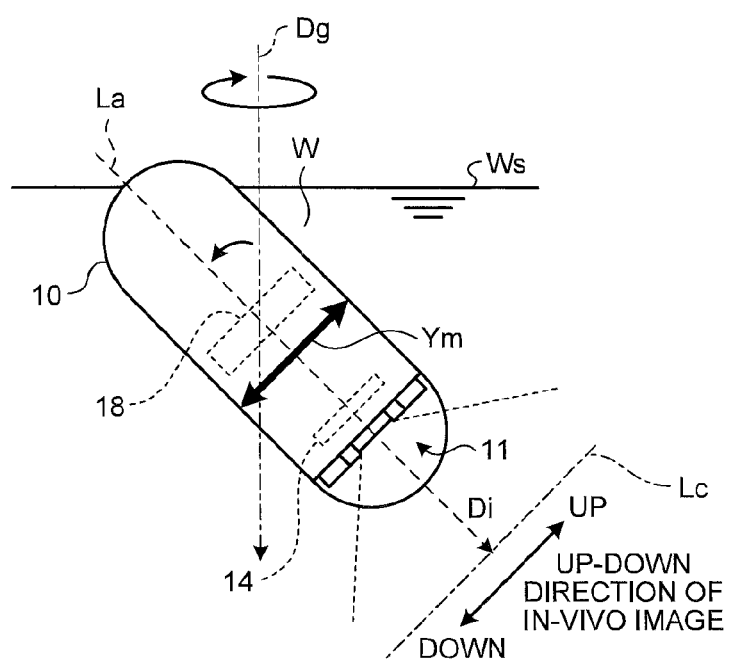
FIG. 5 is a conceptual diagram for describing a state of the capsule endoscope in which liquid is introduced into a subject (a state in which a magnetic field acts)

FIG. 5 is a conceptual diagram for describing a state of the capsule endoscope 10 in which the liquid W is introduced into the subject and illustrates a state in which a magnetic field for controlling an inclination angle of the capsule endoscope 10 acts on the permanent magnet 18. As illustrated in FIG. 5, the inclination of the long axis La of the capsule endoscope 10 with respect to the vertical direction Dg can be controlled by applying a magnetic field from the outside to the permanent magnet 18 of the capsule endoscope 10. For example, by applying a magnetic field in which the direction of the line of magnetic force has an inclination with respect to a horizontal surface to the permanent magnet 18, it is possible to incline the capsule endoscope 10 with respect to the vertical direction Dg so that the magnetization direction Ym of the permanent magnet 18 is approximately parallel to the line of magnetic force. In this case, the posture of the capsule endoscope 10 changes while the magnetization direction Ym maintains a state of being included in the vertical plane.

Therefore, by applying a magnetic field that revolves about the vertical direction Dg in an inclined state of the capsule endoscope 10 to allow the capsule endoscope 10 to revolve around the vertical direction Dg as indicated by an arrow, it is possible to easily acquire the in-vivo image around the capsule endoscope 10.

In the first embodiment, as illustrated in FIG. 3, the permanent magnet 18 is disposed so that the magnetization direction Ym is parallel to the up-down direction Yu of the imaging surface of the imaging element 14. Due to this, the up-down direction of the in-vivo image created based on the image data generated by the imaging element 14 is identical to the direction parallel to the magnetization direction Ym of the permanent magnet 18. Therefore, as illustrated in FIG. 5, the direction of an intersection line Lc between a plane including an imaging direction Di and the vertical direction Dg of the imaging unit 11 and a plane orthogonal to the imaging direction Di is parallel to the up-down direction of the in-vivo image based on the image data generated by the imaging unit 11. Here, the imaging direction Di is an optical-axis direction of an optical system that forms the imaging unit 11.

Referring again to FIG. 1, the guidance device 20 includes a receiving unit 21 that performs wireless communication with the capsule endoscope 10 to receive a radio signal transmitted from the capsule endoscope 10, a position and posture detection unit 22 that detects the position and the posture of the capsule endoscope 10 inside the subject based on the radio signal received by the receiving unit 21, a display unit 23 that acquires an image signal from the radio signal received by the receiving unit 21, applies prescribed signal processing on the image signal to obtain an in-vivo image, displays the in-vivo image on a screen and displays information such as the position and the posture of the capsule endoscope 10 in the subject, a first operation input unit 24 and a second operation input unit 25 that receive the input of information or the like indicating various operations on the capsule medical device guidance system 1, the magnetic field generation unit 26 as a guidance unit that generates a magnetic field for guiding the capsule endoscope 10, a control unit 27 that controls these respective units, and a storage unit 28 that stores image data or the like of the in-vivo image obtained by the capsule endoscope 10.

Figure 6:
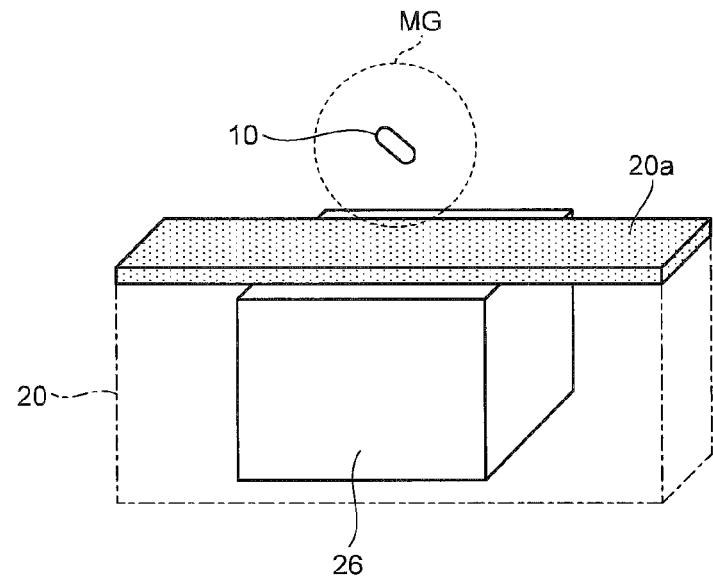
FIG. 6 is a schematic view illustrating a configuration example of an appearance of the guidance device illustrated in FIG. 1.

FIG. 6 is a schematic view illustrating an example of the appearance of the guidance device illustrated in FIG. 1. As illustrated in FIG. 6, a bed 20a as a table on which the subject is mounted is provided in the guidance device 20. At least the magnetic field generation unit 26 that generates the magnetic field MG is disposed under the bed 20a.

The receiving unit 21 includes a plurality of receiving antennas 21a and sequentially receives radio signals from the capsule endoscope 10 via these receiving antennas 21a. The receiving unit 21 selects an antenna in which the received field intensity is the highest among these receiving antennas 21a, performs a demodulation process or the like on the radio signals received from the capsule endoscope 10 via the selected antenna to extract an image signal from the radio signals, and outputs the image signal to the display unit 23.

The position and posture detection unit 22 detects the position and the posture of the capsule endoscope 10 in the subject based on the intensity of the radio signal received by the receiving unit 21 and generates and outputs information on the position and the posture of the capsule endoscope 10. Hereinafter, the information on the position and the posture of the capsule endoscope 10 will be collectively referred to as position information. As an example, as disclosed in Japanese Patent Application Publication No. 2007-283001, the position of the capsule endoscope 10 can be calculated by repeating a process of setting the initial value of the position appropriately and calculating an estimated value of the position according to the Gauss-Newton method until a shift amount between the calculated estimated value and the previously estimated value is equal to or smaller than a prescribed value. Alternatively, the position and the posture of the capsule endoscope 10 may be calculated by providing a coil that generates a high-frequency magnetic field in the capsule endoscope 10 and detecting the magnetic field generated by the coil outside the subject.

The display unit 23 has a screen formed of various displays such as a liquid crystal display and displays the in-vivo image based on the image signal input from the receiving unit 21, the position information of the capsule endoscope 10, and other various types of information on the screen.

The first operation input unit 24 inputs instruction information (guidance instruction information) for changing the position or the posture of the capsule endoscope 10 to the control unit 27 according to an operation externally input by a user. The first operation input unit 24 is realized by an operation table including a joystick, various buttons, and various switches, an input device such as a keyboard, or the like.

Figure 7A:
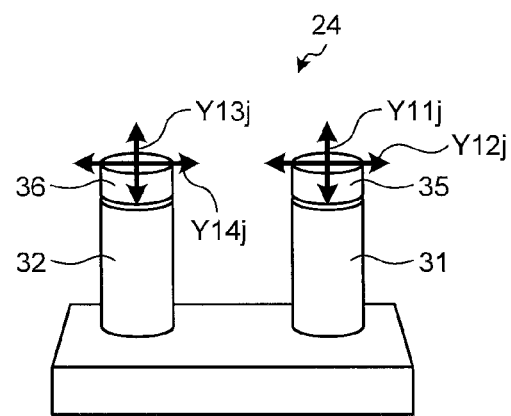
FIGS. 7(a) and 7(b) are diagrams illustrating an example of a first operation input unit illustrated in FIG. 1.
Figure 7B:
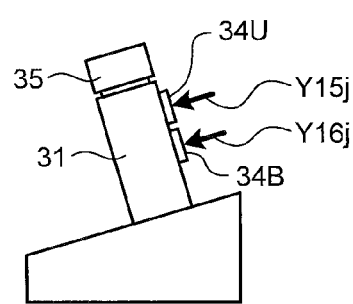
Figure 8:
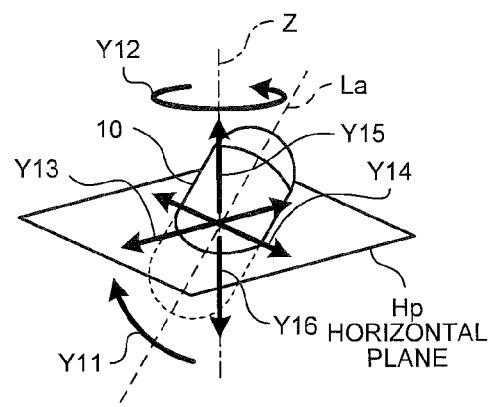
FIG. 8 is a schematic view for describing a change in the position or the posture of a capsule endoscope according to an operation on the first operation input unit illustrated in FIGS. 7(a) and 7(b)

FIGS. 7(a) and 7(b) are schematic views illustrating a configuration example of the first operation input unit 24. FIG. 8 is a schematic view for describing a change in the position or the posture of the capsule endoscope 10 according to an operation on the first operation input unit 24 illustrated in FIGS. 7(a) and 7(b).

In the first embodiment, as illustrated in FIGS. 7(a) and 7(b), the first operation input unit 24 is formed using two joysticks 31 and 32 for three-dimensionally operating the guidance of the capsule endoscope 10 by the magnetic field generation unit 26. The joysticks 31 and 32 can be tilted in an up-down direction and a left-right direction. As illustrated in FIG. 7(a), when the joysticks 31 and 32 are tilted in the directions indicated by arrows Y11j, Y12j, Y13j, and Y14j, the first operation input unit 24 inputs, to the control unit 27, guidance instruction information for moving the capsule endoscope 10 so as to be tilted in the direction indicated by arrow Y11, rotate in the direction indicated by arrow Y12, or move in a direction (within a horizontal plane) indicated by arrows Y13 and Y14 as illustrated in FIG. 8.

As illustrated in FIG. 7(b), an up button 34U and a down button 34B are provided on a back surface of the joystick 31. When the up button 34U is pressed as indicated by arrow Y15j in FIG. 7(b), the first operation input unit 24 inputs, to the control unit 27, guidance instruction information for raising the capsule endoscope 10 along the Z-axis as indicated by arrow Y15 as illustrated in FIG. 8. On the other hand, when the down button 34B is pressed as indicated by arrow Y16j in FIG. 7(b), the first operation input unit 24 inputs, to the control unit 27, guidance instruction information for lowering the capsule endoscope 10 along the Z-axis as indicated by arrow Y16 as illustrated in FIG. 8.

A capture button 35 is provided on an upper portion of the joystick 31. When the capture button 35 is pressed, the first operation input unit 24 inputs, to the control unit 27, instruction information for capturing the in-vivo image displayed on the display unit 23.

Furthermore, an approach button 36 is provided on an upper portion of the joystick 32. When the approach button 36 is pressed, the first operation input unit 24 inputs, to the control unit 27, guidance instruction information for guiding the capsule endoscope 10 so that the side of the capsule endoscope 10 close to the imaging unit 11 approaches an imaging target of the imaging unit 11.

The second operation input unit 25 inputs, to the control unit 27, instruction information (display direction change instruction information) of changing the direction of the in-vivo image displayed on the display unit 23 according to an operation externally input by a user. The second operation input unit 25 includes a button or a switch provided on an operating table and an icon and the like displayed on the display unit 23.

The magnetic field generation unit 26 generates a magnetic field for respectively changing the position, the inclination angle, and the azimuth angle of the capsule endoscope 10 introduced into the subject with respect to the subject. The configuration of the magnetic field generation unit 26 is not particularly limited as long as the magnetic field generation unit 26 can form the magnetic field MG of which the direction of the line of magnetic force can be controlled by the control unit 27 in the area on the bed 20a on which the subject is mounted. For example, the magnetic field generation unit 26 may be formed using an electromagnet, and the magnetic field generation unit 26 may be formed using a permanent magnet and a driving unit that drives the permanent magnet and changes the position and the direction thereof.

The control unit 27 includes a guidance controller 271 that controls the guidance of the capsule endoscope 10 by the magnetic field generation unit 26 and a display controller 272 that controls the display of the in-vivo image and various types of information on the display unit 23.

The guidance controller 271 performs control of guiding the capsule endoscope 10 to a position and a posture desired by the user by controlling the operation of the magnetic field generation unit 26 based on the guidance instruction information input from the first operation input unit 24, the detection result of the position and posture detection unit 22, and the direction of the in-vivo image displayed on the display unit 23.

The display controller 272 allows the display unit 23 to display the in-vivo image and various types of information in a prescribed format and performs control of displaying the in-vivo image acquired by the capsule endoscope 10 on the display unit 23 in a direction desired by the user based on the display direction change instruction information input from the second operation input unit 25.

The storage unit 28 is achieved by using a storage medium that stores information in a rewritable manner, such as a flash memory and a hard disk. The storage unit 28 stores information such as various programs and various parameters used when the control unit 27 controls the components of the guidance device 20 as well as image data of a group of the in-vivo images of the subject, captured by the capsule endoscope 10.

Figure 9:
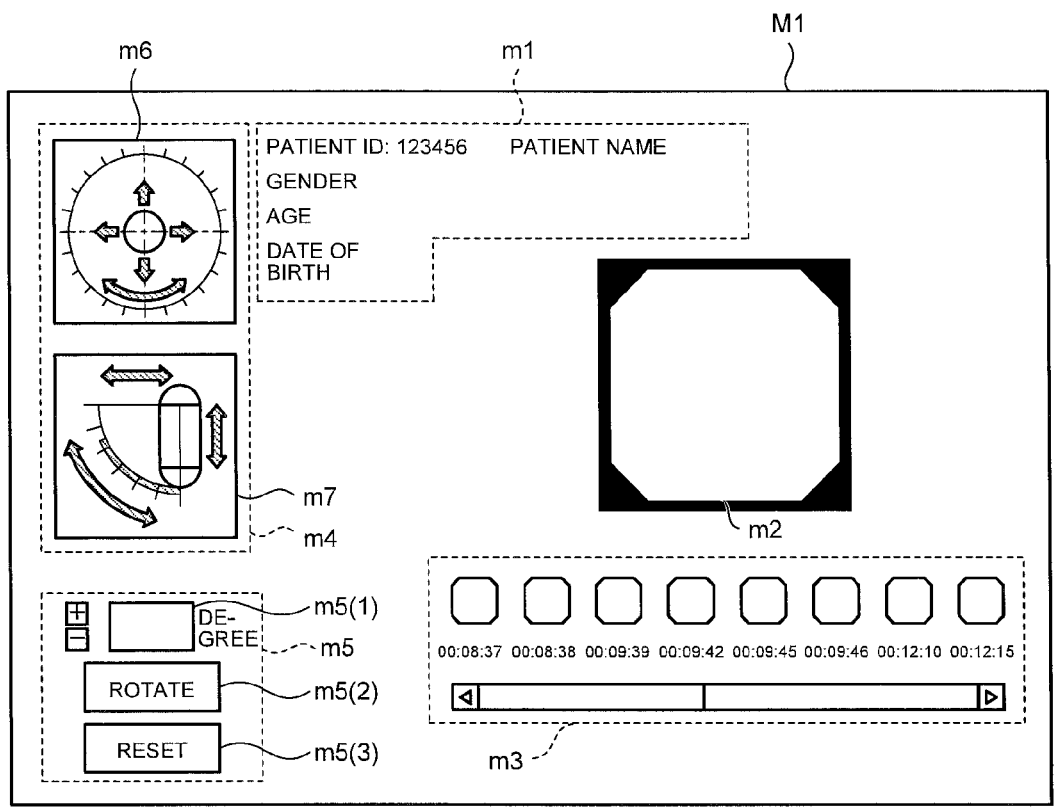
FIG. 9 is a diagram illustrating an example of a screen on which an in-vivo image is displayed.

FIG. 9 is a schematic view illustrating an example of a screen of the display unit 23 on which the in-vivo image is displayed. A screen M1 illustrated in FIG. 9 includes a patient information display area m1 in which information such as a patient ID, a patient name, a patient gender, an age, and the date of birth is displayed, an image display area m2 in which the in-vivo image acquired by the imaging unit 11 is displayed, a capture image display area m3 in which a plurality of in-vivo images captured by a prescribed operation on the first operation input unit 24 are displayed, an operation information display area m4 in which operation information on the capsule endoscope 10 is displayed, and a display direction change operation portion m5 that functions as the second operation input unit 25. In the first embodiment, the four sides of a rectangular in-vivo image are masked as illustrated in the image display area m2.

The image display area m2 is an area in which an in-vivo image is displayed based on the image signal sequentially input from the receiving unit 21. The direction of the in-vivo image in the image display area m2 is set so that the up-down direction of the in-vivo image in an initial state is identical to the up-down direction of the image display area m2 of the screen M1. Here, the up-down direction of the in-vivo image corresponds to the up-down direction of the imaging surface of the imaging element 14 disposed in the capsule endoscope 10.

The operation information display area m4 is an area in which a posture diagram m6 indicating the posture in a vertical plane of the capsule endoscope 10 and a posture diagram m7 indicating the posture in a horizontal plane are displayed. In the posture diagrams m6 and m7, a plurality of directions in which the capsule endoscope 10 can be guided are indicated by arrows. When an operation of guiding the capsule endoscope 10 in a certain direction is input, the display color of an arrow corresponding to the input direction among these arrows is changed. In this way, the guidance operation of the user is assisted.

The guidance instruction information input from the first operation input unit 24 is reflected on a control signal that the guidance controller 271 outputs when controlling the magnetic field generation unit 26. Accordingly, the posture of the capsule endoscope 10 displayed in the posture diagrams m6 and m7 can be considered to be substantially the same as the actual posture of the capsule endoscope 10 in the subject.

The display direction change operation portion m5 is an area in which the user operates when changing the direction of the in-vivo image displayed on the image display area m2. The display direction change operation portion m5 includes an input area m5(1) for inputting the angle when rotating the in-vivo image in the screen M1, a rotate button m5(2) for inputting an in-vivo image rotation instruction, and a reset button m5(3) for inputting an instruction for resetting the direction in which the in-vivo image is displayed to an initial state. The display controller 272 rotates the in-vivo image displayed in the image display area m2 by the input angle around the point of center of the in-vivo image according to the display direction change information input according to the operation on the display direction change operation portion m5.

Figure 10:
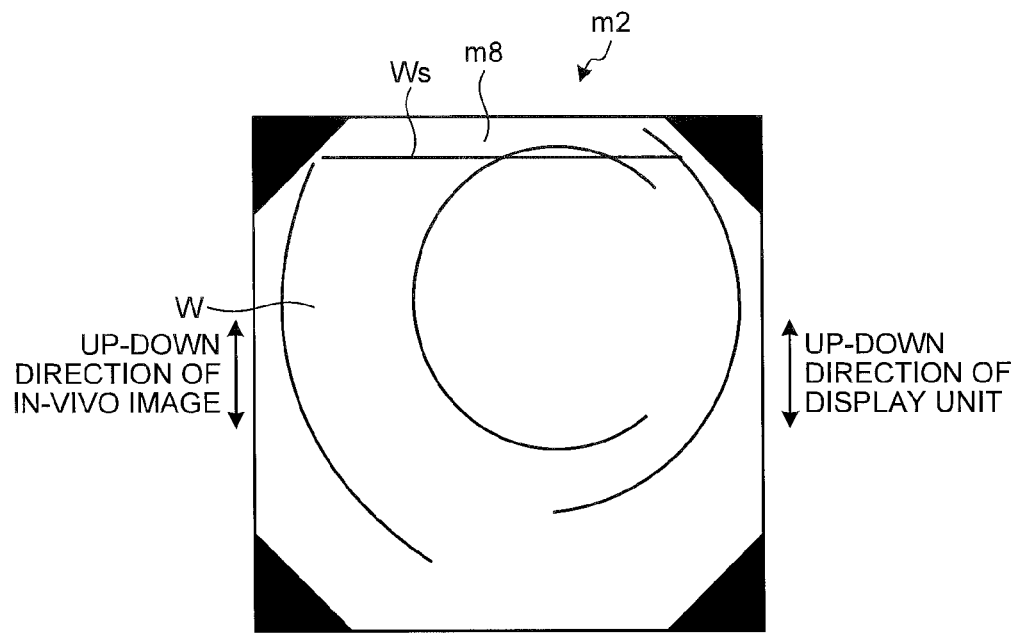
FIG. 10 is a schematic view illustrating an example of an in-vivo image acquired by an imaging unit in the state illustrated in FIG. 5.

For example, as illustrated in FIG. 5, when the capsule endoscope 10 floats near the surface level Ws of the liquid W, in the initial state, the in-vivo image m8 is displayed in the image display area m2 in a direction in which the surface level Ws appearing on the upper side of the imaging visual field of the imaging element 14 is on the upper side as illustrated in FIG. 10.

Figure 11:
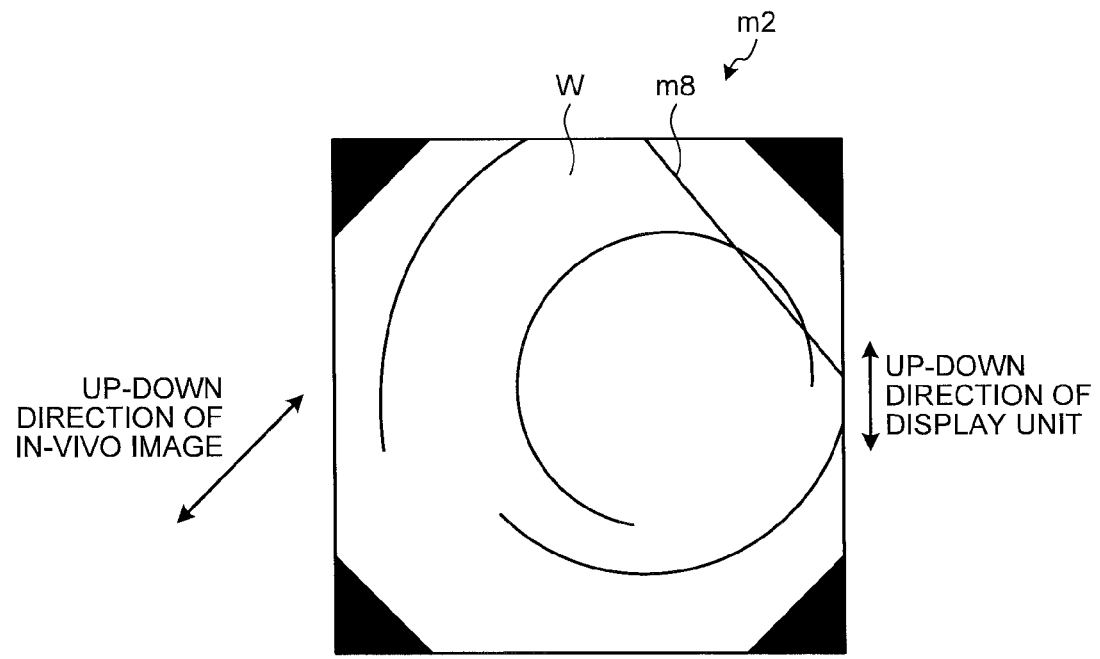
FIG. 11 is a schematic view illustrating an example in which the in-vivo image illustrated in FIG. 10 is rotated by 45°.

In contrast, when a certain angle is input to the input area m5(1) of the second operation input unit 25 and a prescribed pointer operation such as a click operation, for example, is input on the rotate button m5(2), the display controller 272 rotates the in-vivo image m8 by the angle input to the input area m5(1). FIG. 11 illustrates an example in which the in-vivo image m8 illustrated in FIG. 10 is rotated 45° toward the right side (positive direction).

Figure 12A:
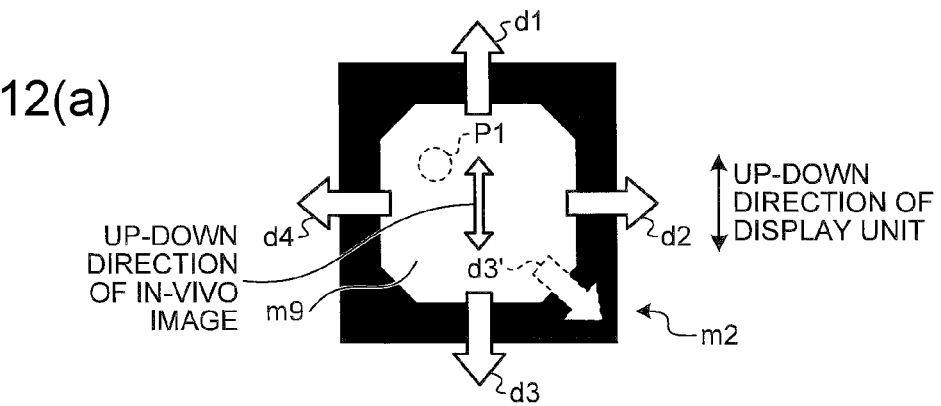
FIGS. 12(a), 12(b) and 12(c) are schematic views for describing guidance control of a capsule endoscope.
Figure 12B:
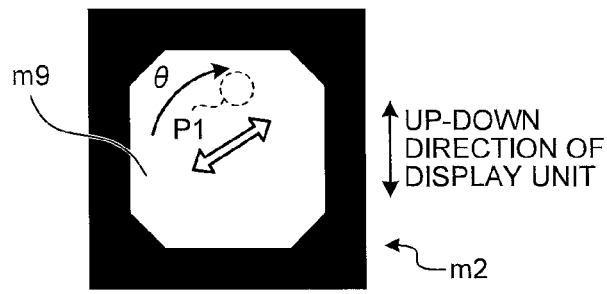
Figure 12C:
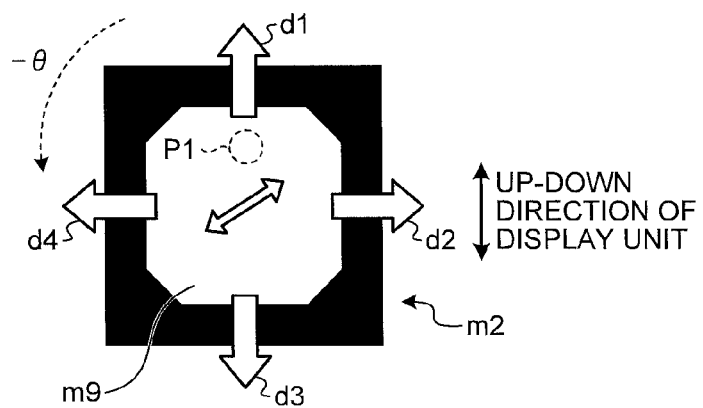

Next, the guidance control of the capsule endoscope 10 according to an operation input to the first operation input unit 24 will be described. FIGS. 12(a), 12(b) and 12(c) are schematic views for describing the guidance control of a capsule endoscope. Among these drawings, FIG. 12(a) illustrates an initial state in which the up-down direction of the in-vivo image m9 is identical to the up-down direction of the image display area m2.

In the initial state, a tilt direction in the up-down direction indicated by arrow Y11j of the joystick 31 illustrated in FIG. 7(a) corresponds to a tilt guidance direction in which the distal end of the capsule endoscope 10 shakes its head so as to pass through the Z-axis on the vertical direction as indicated by arrow Y11 in FIG. 8. When guidance instruction information corresponding to a tilt operation of the joystick 31 indicated by arrow Y11j is input from the first operation input unit 24 to the guidance controller 271, the guidance controller 271 calculates the guidance direction on an absolute coordinate system of the distal end of the capsule endoscope 10 so as to correspond to the tilt direction of the joystick 31 based on the guidance instruction information and calculates a guidance amount so as to correspond to the tilt operation of the joystick 31. Moreover, the guidance controller 271 controls the magnetic field generation unit 26 so as to generate a magnetic field of which the direction of the line of magnetic force is changed according to the calculated guidance direction and guidance amount. As a result, as illustrated in FIG. 12(a), the visual field of the in-vivo image m9 displayed in the image display area m2 within the screen of the display unit 23 can be changed in the direction indicated by arrow d1 or d3.

In the initial state, a tilt direction in the left-right direction indicated by arrow Y12j of the joystick 31 illustrated in FIG. 7(a) corresponds to a rotation guidance direction in which the capsule endoscope 10 orates about the Z-axis as indicated by arrow Y12 in FIG. 8. When guidance instruction information corresponding to a tilt operation of the joystick 31 indicated by arrow Y12j is input from the first operation input unit 24 to the guidance controller 271, the guidance controller 271 calculates a guidance direction on an absolute coordinate system of the distal end of the capsule endoscope 10 so as to correspond to the tilt direction of the joystick 31 based on the guidance instruction information and calculates a guidance amount so as to correspond to the tilt operation of the joystick 31. Moreover, the guidance controller 271 controls the magnetic field generation unit 26 so as to generate a magnetic field of which the direction of the line of magnetic force is changed according to the guidance direction and guidance amount. As a result, as illustrated in FIG. 12(a), the visual field of the in-vivo image m9 displayed in the image display area m2 can be changed in the direction indicated by arrow d2 or d4.

In the initial state, a tilt direction in the up-down direction indicated by arrow Y13j of the joystick 32 illustrated in FIG. 7(a) corresponds to a horizontal backward guidance direction or a horizontal forward guidance direction in which the capsule endoscope 10 advances in a direction in which the long axis La thereof is projected on the horizontal plane Hp as indicated by arrow Y13 in FIG. 8. When guidance instruction information corresponding to a tilt operation of the joystick 32 indicated by arrow Y13j is input from the first operation input unit 24 to the guidance controller 271, the guidance controller 271 calculates the guidance direction and the guidance amount on an absolute coordinate system of the distal end of the capsule endoscope 10 so as to correspond to the tilt direction of the joystick 32 based on the guidance instruction information and controls the magnetic field generation unit 26 so as to generate a magnetic field of which the magnetic field gradient is changed according to the guidance direction and guidance amount. As a result, as illustrated in FIG. 12(a), the visual field of the in-vivo image m9 displayed in the image display area m2 can be changed in the direction indicated by arrow d1 or d3.

In the initial state, a tilt direction in the left-right direction indicated by arrow Y14j of the joystick 32 illustrated in FIG. 7(a) corresponds to a horizontal right guidance direction or a horizontal left guidance direction in which the capsule endoscope 10 advances in a direction in which the long axis La thereof is projected on the horizontal plane Hp as indicated by arrow Y14 in FIG. 8. When guidance instruction information corresponding to a tilt operation of the joystick 32 indicated by arrow Y14j is input from the first operation input unit 24 to the guidance controller 271, the guidance controller 271 calculates the guidance direction and the guidance amount on an absolute coordinate system of the distal end of the capsule endoscope 10 so as to correspond to the tilt direction of the joystick 32 based on the guidance instruction information. In response to this, the magnetic field generation unit 26 generates a magnetic field of which the magnetic field gradient is changed according to the guidance direction and the guidance amount calculated by the guidance controller 271. As a result, the visual field of the in-vivo image m9 illustrated in FIG. 12(a) can be changed to the direction indicated by arrow d2 or d4.

FIG. 12(b) illustrates a state in which the in-vivo image m9 is rotated by a certain angle $\theta$ in relation to the initial state based on the display direction change information input from the second operation input unit 25. In this case, the angle between the up-down direction of the screen M1 (the image display area m2) and the up-down direction of the in-vivo image m9 will be referred to as a display angle $\theta$.

As illustrated in FIG. 12(b), it is assumed that, when the in-vivo image m9 rotates in relation to the initial state, the user performs an operation of changing the visual field of the in-vivo image m9 using the first operation input unit 24. In this case, the user operates the first operation input unit 24 so that the visual field is changed in a desired direction on the image display area m2 while observing the in-vivo image m9 displayed in the image display area m2. Therefore, the direction of an operation that the user performs on the first operation input unit 24 is different from the direction in which the capsule endoscope 10 is actually guided. For example, as illustrated in FIG. 12(c), when a user wants to move a target point P1 in the image display area m2 in the direction indicated by arrow d3, it is necessary to guide the capsule endoscope 10 in a direction corresponding to arrow d3' in the initial state illustrated in FIG. 12(a) in the absolute coordinate system in the subject.

Therefore, when the guidance instruction information is input from the first operation input unit 24, the guidance controller 271 controls the magnetic field generation unit 26 based on the arrangement of the imaging unit 11 in the capsule endoscope 10 and the display angle $\theta$ for rotating the in-vivo image so that the relation between the direction of a change in the visual field of the in-vivo image displayed on the screen M1 (that is, the up-down direction and the left-right direction) and the operation input on the first operation input unit 24 is constant regardless of the display angle $\theta$. Specifically, the guidance controller 271 regenerates guidance instruction information for rotating the tilt direction by an angle $-\theta$ with respect to a tilt operation performed on the joysticks 31 and 32 that form the first operation input unit 24 and calculates the guidance direction and the guidance amount on the absolute coordinate system of the distal end of the capsule endoscope 10 based on the regenerated guidance instruction information. Moreover, the guidance controller 271 causes the magnetic field generation unit 26 to generate a magnetic field of which the magnetic field gradient is changed according to the calculated guidance direction and guidance amount.

For example, when a user inputs an operation of moving the visual field in the direction indicated by arrow d3 illustrated in FIG. 12(c) with respect to the first operation input unit 24, the imaging visual field of the capsule endoscope 10 is guided to be moved in the direction corresponding to arrow d3' illustrated in FIG. 12(a) in the absolute coordinate system in the subject. As a result, an in-vivo image of which the visual field is moved in the direction corresponding to the user's operation (that is, the direction indicated by arrow d3) is displayed in the image display area m2.

As described above, according to the first embodiment of the disclosure, it is possible to rotate the in-vivo image m9 by a desired angle in relation to the initial state and display the in-vivo image on the screen. Moreover, in the initial state, even when the in-vivo image m9 is rotated, the user can operate the first operation input unit 24 with a natural feeling while referring to the in-vivo image m9 without being aware of the direction (that is, the display angle θ) of the in-vivo image m9 and change the imaging visual field in a desired direction.

Second Embodiment

Next, the second embodiment of the disclosure will be described. A capsule medical device guidance system according to the second embodiment has the same configuration as the first embodiment, and an aspect when the in-vivo image displayed on the screen of the display unit 23 is displayed by being rotated in a direction desired by the user is different from the first embodiment.

Figure 13:
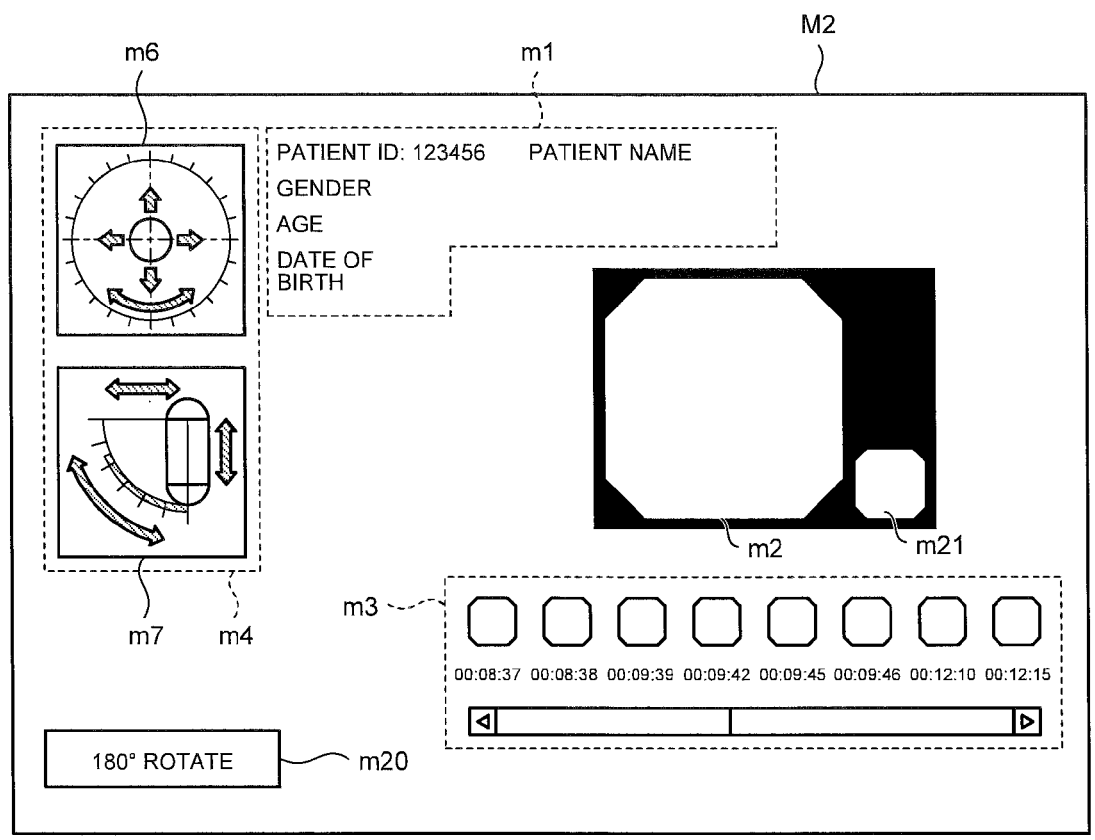
FIG. 13 is a schematic view illustrating an example of a screen on which an in-vivo image is displayed according to a second embodiment of the disclosure.

FIG. 13 is a schematic view illustrating an example of a screen of the display unit 23 of the second embodiment, on which an in-vivo image is displayed. A screen M2 illustrated in FIG. 13 includes a rotate instruction button m20 as the second operation input unit 25 instead of the display direction change operation portion m5 of the screen M1 illustrated in FIG. 9. Moreover, a notification icon m21 for notifying the user of whether the up-down direction of a subject appearing in an in-vivo image being displayed in the image display area m2 is identical to the up-down direction of the screen M2 is displayed near the image display area m2.

The rotate instruction button m20 is an icon that a user operates when changing the direction of the in-vivo image displayed on the screen M2. The display controller 272 rotates the in-vivo image displayed on the screen M2 around the point of center of the in-vivo image in the screen M2 by 180° whenever a prescribed pointer operation such as a click operation, for example, is performed on the rotate instruction button m20.

Figure 14A:
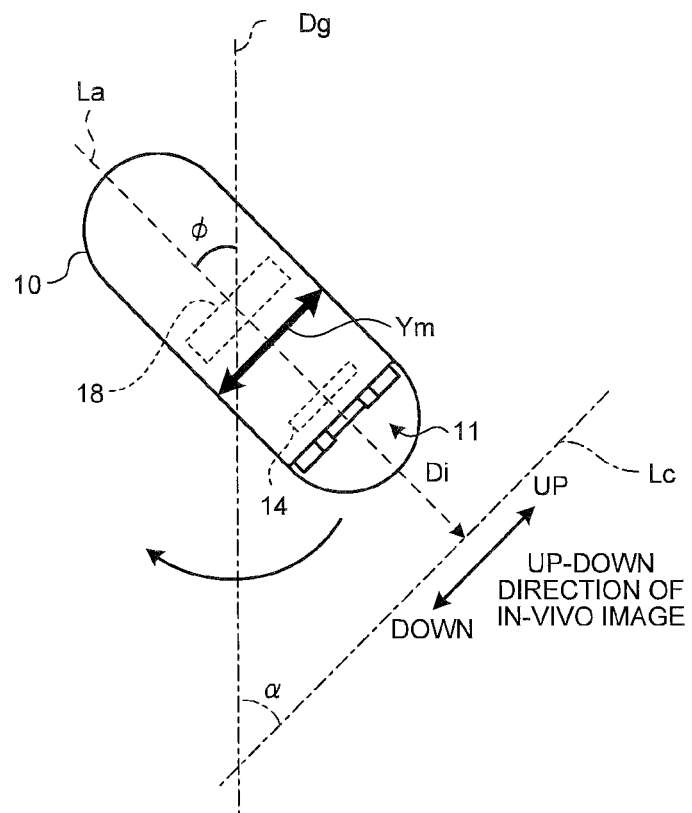
FIGS. 14(a) and 14(b) are schematic views illustrating a change in the direction of an imaging element when an inclination angle of a capsule endoscope is changed.
Figure 14B:
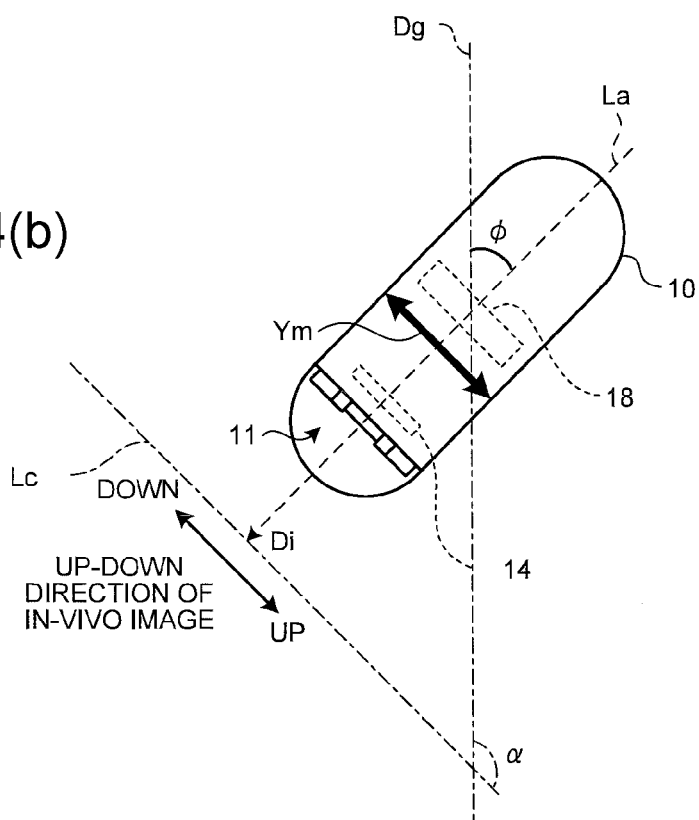

FIGS. 14(a) and 14(b) are schematic views illustrating the imaging visual field of the imaging element 14 corresponding to the inclination angle of the capsule endoscope 10. When an inclination angle φ of the capsule endoscope 10 with respect to the vertical direction Dg is changed from the state illustrated in FIG. 14(a) to the state illustrated in FIG. 14(b), the up-down direction of the imaging surface of the imaging element 14 is inverted with respect to the up-down direction of the vertical direction (that is, the up-down direction of the absolute coordinate system) before and after the inclination angle φ exceeds 0°. As a result, the up-down direction of the subject appearing the in-vivo image is also inverted with respect to the up-down direction of the in-vivo image before and after the inclination angle φ exceeds 0°.

Figure 15A:
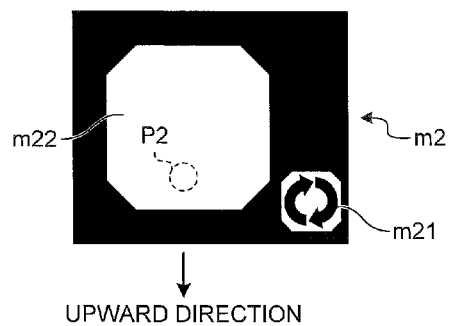
FIGS. 15(a) and 15(b) are schematic views for describing guidance control of a capsule endoscope by a display controller according to the second embodiment.

On the other hand, in the initial state of the display unit 23, the up-down direction of the in-vivo image is set to be identical to the up-down direction of the screen M2. Due to this, when the in-vivo image acquired in the state illustrated in FIG. 14(b) is displayed on the screen M2, as illustrated in FIG. 15(a), the up-down direction of the subject appearing in the in-vivo image is inverted from the up-down direction of the screen M2. In this case, when the user performs a guidance operation on the capsule endoscope 10 using the first operation input unit 24 with the feeling on the absolute coordinate system, the user feels a sense of incongruity.

Here, as illustrated in FIG. 14(b), in order to make the up-down direction of the imaging element 14 identical to the up-down direction of the absolute coordinate system without changing the imaging visual field from the state in which the up-down direction of the imaging element 14 is inverted from the up-down direction of the absolute coordinate system, it is necessary to rotate the capsule endoscope 10 by 180° around the vertical direction Dg after inverting the inclination angle with respect to the vertical direction Dg of the capsule endoscope 10. However, the guidance operation is complex.

Figure 15B:
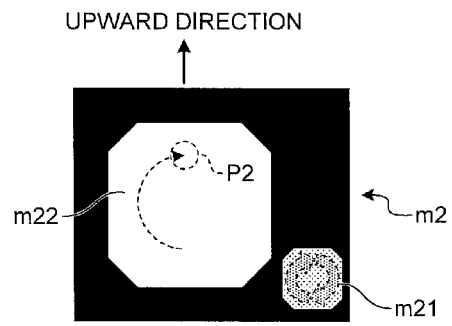

Therefore, in the second embodiment, when the up-down direction of the subject appearing in the in-vivo image in the initial state is inverted from the up-down direction of the screen M2, both up-down directions are made identical by changing the direction of the in-vivo image displayed on the screen M2. FIGS. 15(a) and 15(b) are schematic views for describing the guidance control of the capsule endoscope 10 by the display controller 272.

The display controller 272 determines whether an angle α between a direction indicating the upper side of the imaging element 14 among the directions parallel to the intersection line Lc between a plane including the imaging direction Di and the vertical direction Dg of the imaging unit 11 and a plane orthogonal to the imaging direction Di, and a vertically upward direction is an obtuse angle based on the position information output from the position and posture detection unit 22. When the angle α is an obtuse angle, the display controller 272 determines that, in the initial state, the up-down direction of the subject appearing in the in-vivo image m22 is inverted from the up-down direction of the screen M2 and displays the notification icon m21 on the screen M2 as illustrated in FIG. 15(a). The user can understand that the up-down direction of the subject appearing in the in-vivo image m22 is inverted from the up-down direction of the screen M2 by looking at the notification icon m21. A target point P2 in the in-vivo image m22 illustrated in FIGS. 15(a) and 15(b) indicate a point positioned on the upper side of the subject.

When a user wants to make the up-down direction of the subject appearing in the in-vivo image m22 identical to the up-down direction of the screen M2, the user performs a prescribed pointer operation such as a click operation, for example, on the rotate instruction button m20. The display controller 272 rotates the direction of the in-vivo image by 180° as illustrated in FIG. 15(b) according to the display direction change instruction information input according to the operation on the second operation input unit 25. In this way, it is possible to make the up-down direction of the subject appearing in the in-vivo image m22 identical to the up-down direction of the screen M2. Moreover, in this case, the display controller 272 removes the notification icon m21 displayed on the screen M2. The user can understand that the up-down direction of the subject appearing in the in-vivo image m22 is identical to the up-down direction of the screen M2 by checking that the notification icon m21 is removed.

Moreover, when the direction of the display of the in-vivo image m22 is rotated in relation to the initial state, the guidance controller 271 inverts the guidance direction in the up-down direction and the left-right direction with respect to the guidance instruction information input according to the operation on the first operation input unit 24 such as the joysticks 31 and 32, for example, and then controls the magnetic field generation unit 26 in order to guide the capsule endoscope 10.

As described above, according to the second embodiment of the disclosure, the user can easily understand whether the up-down direction of the subject appearing in the in-vivo image m22 is identical to the up-down direction of the screen M2 by referring to the notification icon m21. Moreover, according to the second embodiment, even when the up-down direction of the subject appearing in the in-vivo image m22 is inverted from the up-down direction of the screen M2, the user can make both directions identical by a simple operation on the second operation input unit 25. Furthermore, according to the second embodiment, when the direction of the display of the in-vivo image m22 in relation to the initial state is rotated by 180°, the guidance controller 271 inverts the guidance direction in the up-down direction and the left-right direction with respect to the guidance instruction information input according to the operation on the first operation input unit 24 and then performs guidance control. Therefore, the user can operate the first operation input unit 24 with a natural feeling while referring to the in-vivo image m22 displayed on the screen M2 and change the imaging visual field of the in-vivo image m22 in a desired direction.

In the second embodiment, although the display of the notification icon m21 is switched to indicate whether the up-down direction of the subject appearing in the in-vivo image m22 is identical to the up-down direction of the screen M2, a display mode of the notification icon m21 may be switched. For example, the color of the notification icon m21 may be switched depending on whether the up-down direction of the subject appearing in the in-vivo image m22 is identical to the up-down direction of the screen M2. Alternatively, when the directions are not identical, the notification icon m21 may blink.

First Modification

Next, the first modification of the first and second embodiments of the disclosure will be described. In the first and second embodiments, an example in which a monocular capsule endoscope 10 having the imaging unit 11 provided at one end of the long axis La is used has been described. However, in the first and second embodiments, a multiocular capsule endoscope in which an imaging unit is provided at both ends (that is, both front and rear sides) of the long axis La may be applied. In this case, the two imaging units may be disposed so that the optical axes of the two imaging units are approximately parallel to or identical to the long axis La of the capsule-shaped casing 100 and the imaging visual fields thereof are directed in opposite directions. That is, the imaging units may be mounted so that the imaging surface of the imaging element included in each imaging unit is orthogonal to the long axis La.

Moreover, in this case, two display areas in which the in-vivo images acquired by the two imaging units are displayed are provided on the screen of the display unit 23 that displays in-vivo images. In each of the display areas, an in-vivo image is displayed in a direction corresponding to a user's operation on the second operation input unit 25 similarly to the first and second embodiments, and the guidance operation of the capsule endoscope is performed by taking the direction of display of the in-vivo image into consideration. As a result, the user can easily understand the correlation between the displayed in-vivo image and the input operation and high operability can be realized.

Second Modification

Next, the second modification of the first and second embodiments of the disclosure will be described. In the first and second embodiments, the information on the position and the posture of the capsule endoscope 10 may be further displayed in correlation with the direction of display of an in-vivo image. In this case, when the direction of display of an in-vivo image is rotated, the display content of the information on the position and the posture of the capsule endoscope 10 is changed so as to correspond to the rotation.

Third Modification

Next, the third modification of the first and second embodiments of the disclosure will be described. In the first and second embodiments, the center of gravity G is set on the long axis La so that the capsule endoscope 10 floats with the long axis La facing the vertical direction in a state in which a magnetic field is not applied and the imaging unit 11 faces the liquid bottom in this state. However, the position of the center of gravity G may be set so that the imaging unit 11 faces the upper side of the liquid level in a state in which a magnetic field is not applied.

Moreover, the position of the center of gravity G may be shifted in a radial direction from the long axis La so that the capsule endoscope 10 floats with the long axis La inclined with respect to the vertical direction in a state in which a magnetic field is not applied. In this case, it is possible to uniquely control the azimuth angle and the inclination angle of the capsule endoscope 10 in the liquid W with respect to the magnetic field generated by the magnetic field generation unit 26.

Furthermore, the specific gravity of the capsule endoscope 10 may be set larger than the specific gravity of the liquid W so that the capsule endoscope 10 is immersed in the water in a state in which a magnetic field is not applied, and the position of the center of gravity G may be set so that the imaging unit 11 faces the liquid bottom or the liquid level.

Fourth Modification

Next, the fourth modification of the first and second embodiments of the disclosure will be described. In the first and second embodiments, although the magnetic field generation unit 26 that generates a magnetic field to be applied to the permanent magnet 18 provided in the capsule endoscope 10 has been used as a guidance unit for the capsule endoscope 10, a guidance system of the capsule endoscope is not limited to the method which uses a magnetic field. For example, a propeller may be provided to the capsule endoscope and the capsule endoscope may be guided by controlling the thrust of the propeller. Alternatively, an ultrasound motor may be provided to the capsule endoscope and the capsule endoscope may be guided by controlling the driving force of the ultrasound motor.

According to some embodiments, the guidance unit is controlled based on the arrangement of the imaging unit in the capsule medical device and the direction of the image displayed on the screen so that the relation between the direction of a change in the visual field of the image displayed on the screen and the operation input on the first operation input unit is constant regardless of the direction of the image. Therefore, a user can easily perform a guidance operation on a capsule medical device while observing an in-vivo image displayed in a desired direction on a screen.

The first and second embodiments described above and the modifications thereof are only examples for implementing the present invention, and the present invention is not limited to these examples. Moreover, various inventions can be invented by appropriately combining a plurality of constituent elements disclosed in the first and second embodiments and the modifications of the present invention. The present invention can be variously modified depending on specifications and the like. Furthermore, it is obvious from the above description that other various embodiments are possible within the scope of the present invention.

What is claimed is:

1. A capsule medical device guidance system for guiding a capsule medical device configured to be introduced into a subject to capture an inside of the subject, the system comprising:
    an image sensor that is fixedly arranged inside the capsule medical device, the image sensor being configured to capture the inside of the subject;
    a guidance device configured to guide the capsule medical device inside the subject;
    a display including a screen on which an image captured by the image sensor is displayed;
    a first operation input device configured to input first instruction information for changing at least one of a position and a posture of the capsule medical device according to an external input operation;
    a second operation input device configured to input second instruction information for rotating within the screen, the image displayed on the screen, around a center of the image according to an external input operation;
    a guidance controller configured to control the guidance device so as to change at least one of the position and the posture of the capsule medical device, based on the first instruction information; and
    a display controller configured to control a direction of the image displayed on the screen based on the second instruction information, wherein
    when the first instruction information is input, the guidance controller is configured to control the guidance device, based on an arrangement of the image sensor in the capsule medical device and the direction of the image displayed on the screen, so that a relation between a direction of a change in a visual field of the image displayed on the screen and an operation input that is input on the first operation input device is constant regardless of the direction of the image.

2. The capsule medical device guidance system according to claim 1, wherein the display controller is configured to rotate the image by a predetermined angle around the center of the image when the second instruction information is input from the second operation input device.

3. The capsule medical device guidance system according to claim 2, wherein the predetermined angle is 180°.

4. The capsule medical device guidance system according to claim 1, wherein
    the display controller is configured to:
        determine whether an angle between a direction orthogonal to a imaging direction of the image sensor and indicating an upper side of the image sensor and a vertically upward direction is an obtuse angle; and
        if the angle is determined to be the obtuse angle, display a notification icon on the screen, and if the angle is determined not to be the obtuse angle, hide the notification icon on the screen or display, on the screen, a notification icon different from the notification icon when the angle is determined to be the obtuse angle.

5. The capsule medical device guidance system according to claim 1, wherein
    the capsule medical device includes a permanent magnet,
    a center of gravity of the capsule medical device is shifted from a geometric center of the capsule medical device in a direction different from a magnetization direction of the permanent magnet,
    the image sensor is fixed to the capsule medical device so as to capture in the direction different from the magnetization direction, and
    the guidance device is configured to guide the capsule medical device by generating a magnetic field.

6. A capsule medical device guidance system for guiding a capsule medical device configured to be introduced into a subject to capture an inside of the subject, the system comprising:
    an image sensor that is fixedly arranged inside the capsule medical device, the image sensor being configured to capture the inside of the subject;
    a guidance device configured to guide the capsule medical device inside the subject;
    a display including a screen on which an image captured by the image sensor is displayed;
    a first operation input device configured to input first instruction information for changing at least one of a position and a posture of the capsule medical device according to an external input operation;
    a guidance controller configured to control the guidance device so as to change at least one of the position and the posture of the capsule medical device, based on the first instruction information; and
    a display controller configured to:
        determine whether an angle between a direction orthogonal to a imaging direction of the image sensor and indicating an upper side of the image sensor and a vertically upward direction is an obtuse angle; and
        if the angle is determined to be the obtuse angle, display a notification icon on the screen, and if the angle is determined not to be the obtuse angle, hide the notification icon on the screen or display, on the screen, a notification icon different from the notification icon when the angle is determined to be the obtuse angle.

7. The capsule medical device guidance system according to claim 6, further comprising:
    a second operation input device configured to input second instruction information for rotating within the screen, the image displayed on the screen, around a center of the image according to an external input operation, wherein when the second instruction information is input from the second operation input device;
the display controller is configured to rotate the image by a predetermined angle around the center of the image; and
the guidance controller is configured to invert a direction for changing at least one of the position and the posture of the capsule medical device in an up-down direction and a left-right direction with respect to the first instruction information input from the first operation input device.

8. The capsule medical device guidance system according to claim 7, wherein the predetermined angle is 180°.

9. The capsule medical device guidance system according to claim 7, wherein the display controller is configured to switch display of the notification icon when the second instruction information is input.

10. The capsule medical device guidance system according to claim 6, wherein
the capsule medical device includes a permanent magnet,
a center of gravity of the capsule medical device is shifted from a geometric center of the capsule medical device in a direction different from a magnetization direction of the permanent magnet,
the image sensor is fixed to the capsule medical device so as to capture in the direction different from the magnetization direction, and
the guidance device is configured to guide the capsule medical device by generating a magnetic field.

\* \* \* \* \*